(12) United States Patent
Song et al.

(10) Patent No.: US 9,134,276 B2
(45) Date of Patent: Sep. 15, 2015

(54) BULK ACOUSTIC WAVE RESONATOR SENSOR

(75) Inventors: In Sang Song, Osan-si (KR); Sang Uk Son, Yongin-si (KR); Jea Shik Shin, Hwaseong-si (KR); Hyung Rak Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 735 days.

(21) Appl. No.: 13/232,087

(22) Filed: Sep. 14, 2011

(65) Prior Publication Data

US 2012/0068690 A1    Mar. 22, 2012

(30) Foreign Application Priority Data

Sep. 16, 2010 (KR) .................. 10-2010-0090835

(51) Int. Cl.
| | |
|---|---|
| *G01N 29/30* | (2006.01) |
| *G01N 29/02* | (2006.01) |
| *G01R 23/02* | (2006.01) |
| *G01N 29/036* | (2006.01) |

(52) U.S. Cl.
CPC ............ *G01N 29/022* (2013.01); *G01N 29/036* (2013.01); *G01N 29/30* (2013.01); *G01R 23/02* (2013.01); *G01N 2291/0255* (2013.01); *G01N 2291/0256* (2013.01); *G01N 2291/0426* (2013.01)

(58) Field of Classification Search
CPC . G01N 29/30; G01N 2291/0426; G01R 23/02
USPC ..................................... 324/76.39; 73/514.34
See application file for complete search history.

(56) References Cited

U.S. PATENT DOCUMENTS

| | | | | |
|---|---|---|---|---|
| 2003/0011382 | A1* | 1/2003 | Chow et al. | 324/601 |
| 2003/0085719 | A1* | 5/2003 | Yoon et al. | 324/663 |
| 2003/0218518 | A1* | 11/2003 | Lee | 333/189 |
| 2004/0150296 | A1* | 8/2004 | Park et al. | 310/324 |
| 2005/0128027 | A1* | 6/2005 | Song et al. | 333/133 |
| 2005/0285604 | A1* | 12/2005 | Shinohara et al. | 324/557 |
| 2009/0277271 | A1 | 11/2009 | Seppa et al. | |
| 2009/0291509 | A1* | 11/2009 | Wakamatsu | 436/543 |

FOREIGN PATENT DOCUMENTS

| | | |
|---|---|---|
| KR | 10-2004-0067661 | 7/2004 |
| KR | 10-2004-0095819 | 11/2004 |
| KR | 10-2008-0027288 | 3/2008 |

* cited by examiner

*Primary Examiner* — Jeff Natalini
(74) *Attorney, Agent, or Firm* — NSIP Law

(57) ABSTRACT

A bulk acoustic wave resonator (BAWR) sensor is provided. The BAWR sensor includes a signal BAWR that measures a resonance frequency that is modified due to a reaction with a target material, a reference BAWR that measures a reference resonance frequency without reaction with an external environment, and a sensing unit that senses the target material, based on the modified resonance frequency and the reference resonance frequency.

24 Claims, 16 Drawing Sheets

BULK ACOUSTIC WAVE RESONATOR SENSOR

CROSS-REFERENCE TO RELATED APPLICATION(S)

This application claims the benefit under 35 U.S.C. §119(a) of Korean Patent Application No. 10-2010-0090835, filed on Sep. 16, 2010, in the Korean Intellectual Property Office, the entire disclosure of which is incorporated herein by reference for all purposes.

BACKGROUND

1. Field

The following description relates to a bulk acoustic wave resonator sensor.

2. Description of Related Art

Demand for a small size sensor, which is capable of sensing various types of samples, has increased. A surface acoustic wave (SAW) sensor has a low quality factor (Q) and a low sensitivity, and is difficult to reduce in size. Thus, arrangement and integration of a SAW sensor may not be appropriate. Accordingly, the SAW sensor may not be the appropriate sensor to be used.

SUMMARY

According to an aspect, a bulk acoustic wave resonator (BAWR) sensor is provided. The BAWR sensor includes a signal BAWR that measures a resonance frequency that is modified due to a reaction with a target material, a reference BAWR that measures a reference resonance frequency without reaction with an external environment, and a sensing unit that senses the target material, based on the modified resonance frequency and the reference resonance frequency.

The signal BAWR may include a first substrate, a first bulk acoustic wave resonance unit comprising a first air cavity formed on a top of the first substrate, and a first lower portion electrode, a first piezoelectric layer, a first upper portion electrode, and a coated layer, which are laminated on a top of the first air cavity, a second substrate comprising a second air cavity formed on a predetermined area of a lower side of the second substrate, and connected to the first substrate, a first in-channel and out-channel unit through which a sample including the target material flows in and out, and a first resonance frequency measuring unit configured to measure a resonance frequency modified by the sample, using the first lower portion electrode and the first upper portion electrode. The reference BAWR may include a third substrate, a second bulk acoustic wave resonance unit including a third air cavity formed on a top of the third substrate and a second lower portion electrode, a second piezoelectric layer, and a second upper portion electrode which are laminated on a top of the third air cavity, a fourth substrate comprising a fourth air cavity formed on a predetermined area of a lower side of the fourth substrate, and connected to the third substrate, and a second resonance frequency measuring unit configured to measure the reference resonance frequency using the second lower portion electrode and the second upper portion electrode.

The coated layer may be coated with a base material configured to react with the target material to sense the target material from the sample.

The coated layer may be located on the top of the first upper portion electrode or under the first lower portion electrode.

The reference acoustic wave resonator may further include a second in-channel and out-channel unit through which the sample including the target material flows in and out.

The first substrate may include a via-hole formed in a predetermined area of a lower side of the first substrate, and the third substrate may include a via-hole formed in a predetermined area of a lower side of the third substrate, the first resonance frequency measuring unit may be connected to the first lower portion electrode and the first upper portion electrode through an electrode pad located under the via-hole, and the second resonance frequency measuring unit may be connected to the second lower portion electrode and the second upper portion electrode through an electrode pad located under the via-hole.

The first in-channel and out-channel unit may be further configured to allow the sample to flow in and out from an external side to the second air cavity, through a hole formed on the second substrate.

The first in-channel and out-channel unit may be further configured to allow the sample to flow in and out from an external side to the first air cavity, through a via-hole formed on the first substrate corresponding to a lower portion of the first air cavity.

The first resonance frequency measuring unit may be connected to the first lower portion electrode and the first upper portion electrode that are formed by patterning a conductive material on the top of the first substrate and an external side of the second substrate, and the second resonance frequency measuring unit may be connected to the second lower portion electrode and the second upper portion electrode that are formed by patterning a conductive material on the top of the third substrate and an external side of the fourth substrate.

The second substrate may include a transparent material so that occurrence of a reaction in the coated layer and an intensity of the reaction are monitored.

The first substrate and the second substrate may be connected to each other based on an anodic bonding scheme or a eutectic bonding scheme.

The signal BAWR may include a first bulk acoustic wave resonance unit comprising a first air cavity formed on a top of the first substrate and a first lower portion electrode, a first piezoelectric layer, a first upper portion electrode, and a coated layer which are sequentially laminated on a top of the first air cavity, and a first resonance frequency measuring unit may be configured to measure the modified resonance frequency using the first lower portion electrode and the first upper portion electrode, and the reference BAWR may include a second bulk acoustic wave resonance unit comprising a second air cavity formed on the top of the first substrate and a second lower portion electrode, a second piezoelectric layer, a second upper portion electrode which are sequentially laminated on a top of the second air cavity, and a second resonance frequency measuring unit configured to measure the reference resonance frequency using the second lower portion electrode and the second upper portion electrode. The signal BAWR and the reference BAWR may include a second substrate comprising a third air cavity formed on a predetermined area of a lower side of the second substrate and connected with the first substrate, and an in-channel and out-channel unit through which a sample including a target material flows in and out.

The first substrate may include a via-hole formed on a predetermined area of a lower side of the first substrate, the first resonance frequency measuring unit may be connected to the first lower portion electrode and the first upper portion electrode, through an electrode pad located under the via-hole, and the second resonance frequency measuring unit may be connected to the second lower portion electrode and the second upper portion electrode, through the electrode pad located under the via-hole.

The in-channel and out-channel unit may be further configured to allow the sample to flow in and out from an external side to the third air cavity through a hole formed on the second substrate.

The in-channel and out-channel unit may be further configured to allow the sample to flow in and out from an external side to the first air cavity through a via-hold formed on the first substrate corresponding to a lower portion of the first air cavity.

The first resonance frequency measuring unit may be connected to the first lower portion electrode and the first upper portion electrode that are formed by patterning a conductive material on the top of the first substrate and an external side of the second substrate, and the second resonance frequency measuring unit may be connected to the second lower portion electrode and the second upper portion electrode that are formed by patterning a conductive material on the top of the first substrate and the external side of the second substrate.

The signal BAWR may include a first substrate, a first bulk acoustic wave resonance unit including a first air cavity formed on a top of the first substrate and a first lower portion electrode, a first piezoelectric layer, a first upper portion electrode, and a coated layer which are sequentially laminated on a top of the first air cavity, and a first resonance frequency measuring unit configured to measure a resonance frequency that is modified by an external environment, through the first lower portion electrode and the first upper portion electrode, and the reference BAWR may include a third substrate, a second BAWR comprising a second air cavity formed on a top of the third substrate and a second lower portion electrode, a second piezoelectric layer, and a second upper portion electrode which are sequentially laminated on a top of the second air cavity, a fourth substrate comprising a third air cavity formed on a predetermined area of the fourth substrate, and connected to the third substrate, and a second resonance frequency measuring unit configured to measure the reference resonance frequency, through the second lower portion electrode and the second upper portion electrode.

The first substrate may include a hole, corresponding to the first air cavity, formed based on an etching scheme so that an overall area of the signal BAWR is exposed to the external environment.

The signal BAWR may include a first bulk acoustic wave resonance unit including a first air cavity formed on a top of a first substrate and a first lower portion electrode, a first piezoelectric layer, a first upper portion electrode, and a coated layer which are sequentially laminated on a top of the first air cavity, and a first resonance frequency measuring unit configured to measure the modified resonance frequency, through the first lower portion electrode and the first upper portion electrode, and the reference BAWR may include a second bulk acoustic wave resonance unit including a second air cavity formed on the top of the first substrate and a second lower portion electrode, a second piezoelectric layer, and a second upper portion electrode which are sequentially laminated on a top of the second air cavity, a second substrate including a third air cavity formed on a predetermined area of a lower side of the second substrate, and connected to the first substrate so that the second bulk acoustic sound resonance unit is isolated from the external environment, and a second resonance frequency measuring unit configured to measure the reference resonance frequency, through the second lower portion electrode and the second upper portion electrode.

The sensing unit may include a database unit configured to store predetermined information corresponding to the modified resonance frequency, and a matching unit configured to match the modified resonance frequency and the stored predetermined information.

The signal BAWR may include an in-channel and out-channel unit through which a sample including a target material including a plurality of characteristics flows in and out, a first bulk acoustic wave resonance unit comprising a first air cavity formed on a top of a first substrate so as to detect a first characteristic of the target material and a first lower portion electrode, a first piezoelectric layer, a first upper portion electrode, and a first coated layer which are sequentially laminated on a top of the first air cavity, a second bulk acoustic wave resonance unit including a second air cavity formed on the top of the first substrate so as to detect a second characteristic of the target material and a second lower portion electrode, a second piezoelectric layer, a second upper portion electrode, and a second coated layer which are sequentially laminated on a top of the second air cavity, a first resonance frequency measuring unit configured to measure a first resonance frequency modified by the sample, through the first lower portion electrode and the first upper portion electrode, and a second resonance frequency measuring unit configured to measure a second resonance frequency modified by the sample, through the second lower portion electrode and the second upper portion electrode, and the sensing unit may detect the first characteristic of the target material based on the first resonance frequency, and detects the second characteristic of the target material based on the second resonance frequency.

The sensing unit may be further configured to sense the target material based on a difference between the modified resonance frequency and the reference resonance frequency exceeding a predetermined value.

The first lower portion electrode, the first piezoelectric layer, the first upper portion electrode, and the coated layer may be sequentially laminated on the top of the first air cavity, and the second lower portion electrode, the second piezoelectric layer, and the second upper portion electrode may be sequentially laminated on the top of the third air cavity.

In another aspect, an analysis device is provided. The analysis device includes a bulk acoustic wave resonator (BAWR) sensor unit including a signal BAWR configured to measure a resonance frequency that is modified due to a reaction with a target material, and a reference BAWR configured to measure a reference resonance frequency without reaction with the target material, and a sensing unit configured to sense the target material, based on the modified resonance frequency and the reference resonance frequency.

Other features and aspects may be apparent from the following detailed description, the drawings, and the claims.

Figure 1:
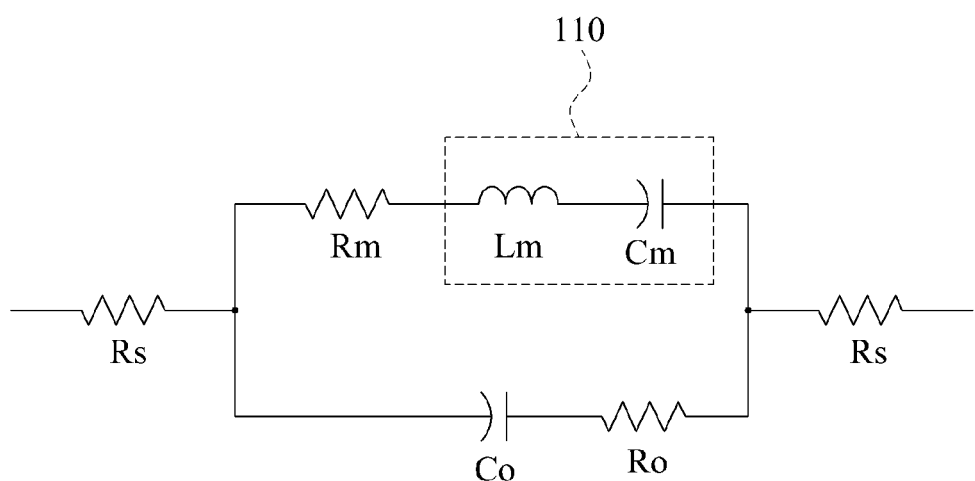
FIG. 1 is a diagram illustrating an example of an equivalent circuit of a bulk acoustic wave resonator (BAWR) in a BAWR sensor.

Throughout the drawings and the detailed description, unless otherwise described, the same drawing reference numerals should be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness. Here, a bulk acoustic wave resonator (BAWR) may operate through electrodes located on an upper portion and a lower portion of a piezoelectric layer. In other words, in response to a high frequency electric potential being provided to the electrodes, the piezoelectric layer may oscillate. Thus, the BAWR may operate as a filter.

In this instance, the BAWR may correspond to a device that induces oscillation or waves of a predetermined frequency using resonance, and the device may be used as a component in a resonance frequency (RF) device. Examples of RF devices include a filter and an oscillator.

FIG. 1 illustrates an example of an equivalent circuit of a BAWR in a BAWR sensor.

The BAWR may have a significantly higher quality factor (Q) than the Q for a SAW sensor. When Q is significantly high, a higher output value may be obtained in a narrow frequency band than when Q is low. Accordingly, when the BAWR is used instead of a SAW sensor, a sensing effect in a predetermined frequency range may be improved. In this instance, power expended for a sensing process in the predetermined frequency range may be reduced in comparison to power expended in the SAW sensor. Thus, power consumption in a total sensing system may be reduced.

The BAWR uses an elastic wave of a piezoelectric material. In response to an RF signal being applied to the piezoelectric material, a mechanical oscillation may occur in a vertical direction of a thickness of a piezoelectric film, and an elastic wave may be generated. An example of the piezoelectric material includes aluminum nitride (AlN). Resonance may occur in response to half the wavelength of the provided RF signal being substantially equal to the thickness of the piezoelectric film. In response to the resonance occurring, electric impedance may significantly change. Thus, a BAWR may be used as a filter to select a frequency. A resonance frequency may be determined based on the thickness of the piezoelectric film, an electrode wrapping the piezoelectric film, an intrinsic elastic wave velocity of the piezoelectric film, and the like. Accordingly, as the thickness of the piezoelectric film decreases, a magnitude of the resonance frequency becomes greater.

Referring to FIG. 1, Rs relates to an ohmic loss due to an electrode, Ro relates to a basic resistance, and Co relates to a static capacitor. In other words, the static capacitor may correspond with a capacity of a resonator. Lm, Cm, and Rm relate to inductance values which vary based on a surrounding environment. For example, a resonance frequency may vary based on a product of Lm and Cm 110, and may vary based on a physical thickness, a material property, a mass, a temperature, and other features associated with a material including an electrode. Therefore, a change in the surrounding environment may be sensed based on a measurement of a change in resonance frequency.

As one example, the BAWR may be used as a pressure sensor. In this example, the resonance frequency of the BAWR may be determined based on a thickness of the BAWR, a mass-density of the BAWR, an elastic constant of material, and the like. In response to an external pressure changing while a predetermined pressure is maintained along a film of the BAWR, a stress may be provided to the BAWR. A change in the stress may cause a change in a strain of the BAWR, and the change in the strain of the BAWR may cause a change in the thickness of the resonator, a change in the mass-density of the resonator, and a change in the elastic constant. Accordingly, the resonance frequency may change due to a change in the external pressure. The BAWR may sense a change in the external pressure by measuring a change in the resonance frequency.

As another example, the BAWR may be used as a temperature sensor. In this example, in response to a change in an external temperature of the BAWR, a thermal stress may occur in the film of the BAWR. The change in the temperature may also cause a change in an internal electric property of the BAWR, so that the BAWR may also measure the change in the temperature by measuring the change in the internal electric property of the BAWR.

Figure 2A:
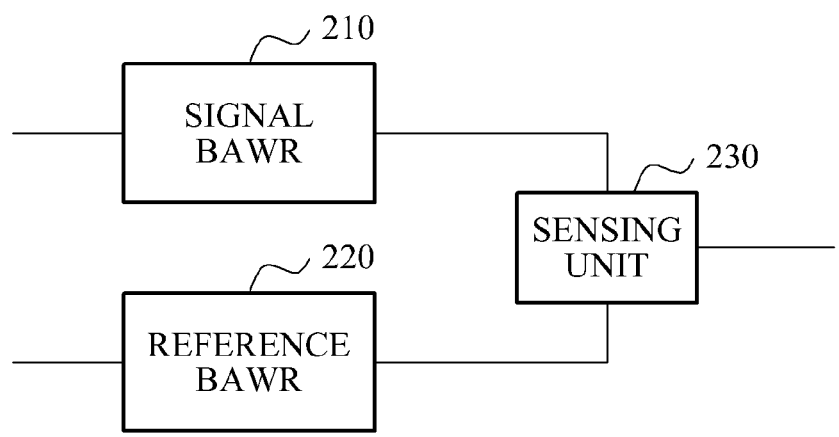
FIG. 2A is a diagram illustrating an example of a BAWR sensor.

FIG. 2A illustrates an example of a BAWR sensor.

Referring to FIG. 2A, the BAWR sensor includes a signal BAWR 210, a reference BAWR 220, and a sensing unit 230.

As an example, the signal BAWR 210 may measure at least one resonance frequency changed due to a reaction with a target material. That is, in response to a sample injected from an external side reacting with a coated layer, the signal BAWR 210 may measure a changed resonance frequency. In the example, the reaction between the sample and the coated layer may affect a physical thickness, a material property, and the like associated with the signal BAWR 210. Thus, the reaction may cause a change in impedance. Since the impedance may be changed, the resonance frequency may change. In this example, in response to a plurality of coated layers capable of reacting with the target material being provided, the signal BAWR 210 may sense different elements by sensing a change in a physical thickness, a material property, a mass, and a temperature associated with materials of the signal BAWR 210. Furthermore, the signal BAWR 210 may aid in pharmaceutical component analysis. In this instance, the signal BAWR 210 may measure a changed resonance frequency, which changes in response to an antigen-antibody reaction. The changed resonance frequency is compared to a reference resonance frequency measured in a buffer or a solution including an antigen without the antibody. In this example, a fluid characteristic and a flow velocity of the buffer or the solution may change due to the antigen-antibody reaction. Thus, the resonance frequency may change in response to the antigen-antibody reaction occurring.

Furthermore, the reference BAWR 220 may measure the reference resonance frequency where no antigen-antibody reaction occurs. In other words, no antigen-antibody reaction occurs may corresponds to without a reaction occurring with an external environment. Here, the reference resonance frequency may be measured without effect from variables, and the reference resonance frequency may be used as a basis for comparison. Subsequently, in response to the reference BAWR 220 being used for pharmaceutical component analysis, the reference BAWR 220 may measure the reference resonance frequency in a buffer including only an antigen before an antibody is injected into the buffer, so that the reference resonance frequency may be compared to the changed resonance frequency which changes due to the antigen-antibody reaction in the buffer. In response to the reference BAWR 220 sensing a change in a pressure, a temperature, and the like, the reference BAWR 220 may measure the reference resonance frequency before a change occurs.

The sensing unit 230 may sense a target material, based on a comparison of at least one changed resonance frequency measured by the signal BAWR 210 and at least one reference resonance frequency measured by the reference BAWR 220. The sensing unit 230 may compare a changed resonance frequency and a corresponding reference resonance frequency. The target material may be sensed when a difference in resonance frequencies is greater than or equal to a predetermined value. In the following example, information associated with the changed resonance frequency and the reference resonance frequency and the associated information may be stored together in a database unit (not illustrated). For example, information associated with changes in a resonance frequency based on one or more various types of antigen-antibody reactions may be stored in the database unit (not illustrated) in advance, for pharmaceutical component analysis. Subsequently, the sensing unit 230 may compare a measured resonance frequency with the data stored in the database unit (not illustrated) and thus, the sensing unit 230 may sense a corresponding type of the antigen-antibody reaction. In this example, the sensing unit 230 may include a matching unit (not illustrated) to match information corresponding to the measured resonance frequency and a value stored in the database.

Figure 2B:
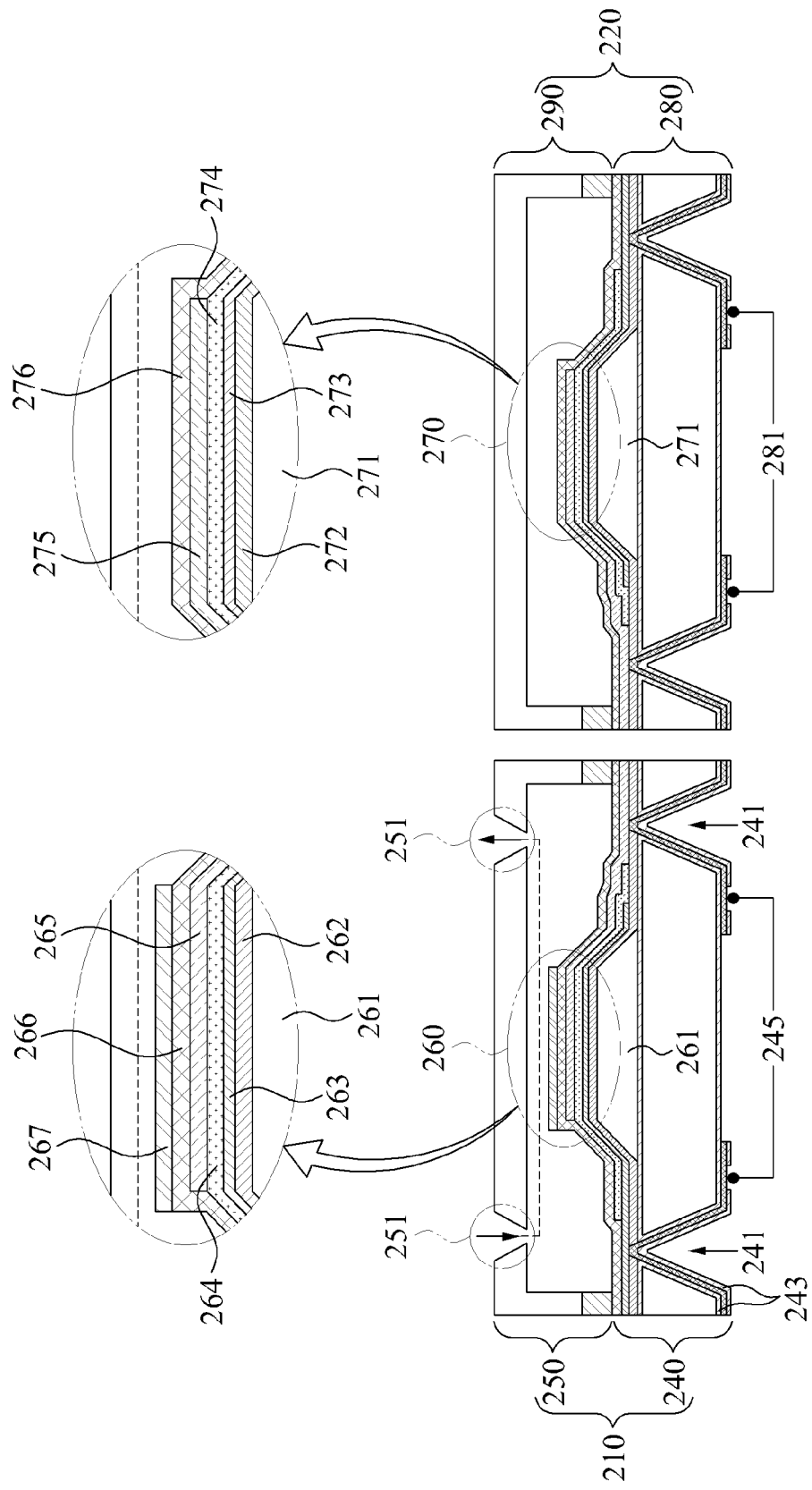
FIGS. 2B through 2D are diagrams illustrating an example of a structure of a BAWR sensor.
Figure 2C:
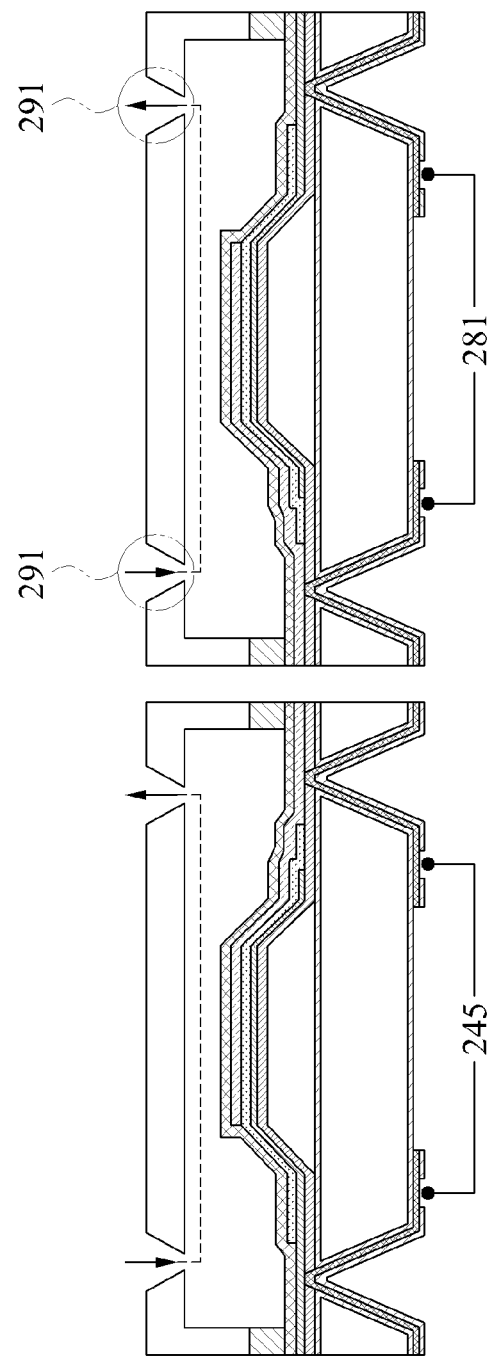
Figure 2D:
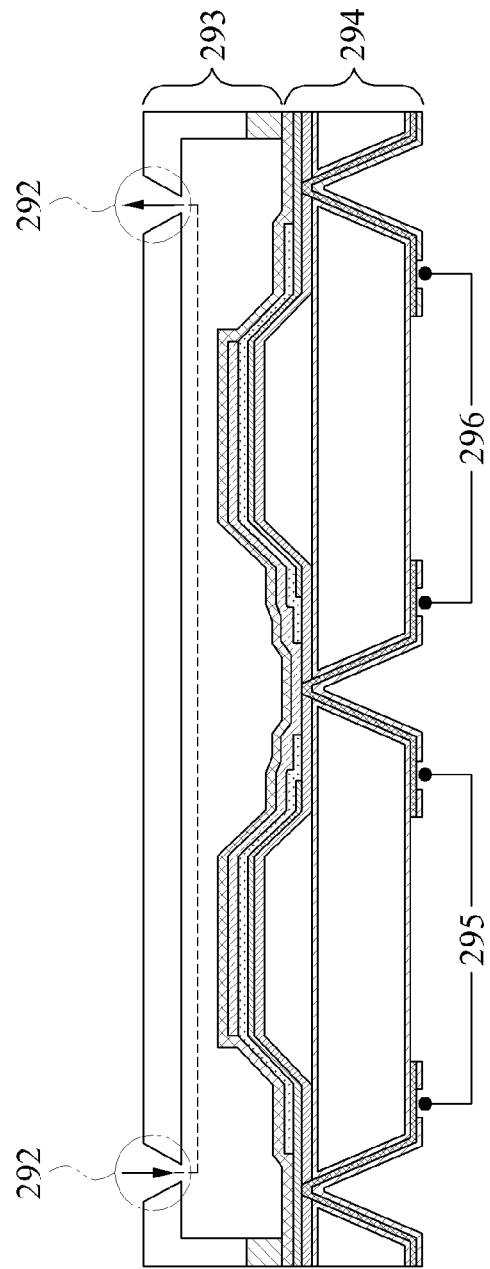

FIGS. 2B through 2D illustrate a structure of a BAWR sensor according to example embodiments.

Referring to FIG. 2B, the signal BAWR 210 and the reference BAWR 220 are included in different substrates, which are separate from each other.

Referring to FIG. 2B, the signal BAWR 210 includes a first substrate 240, a second substrate 250, a first bulk acoustic wave resonance unit 260, a first in-channel and out-channel unit 251, and a first resonance frequency measuring unit 245.

The signal BAWR 210 may measure a changed resonance frequency based on the first resonance frequency measuring unit 245, in response to a coated layer 267 of the first bulk acoustic wave resonance unit 260 reacting with a sample injected through the first in-channel and out-channel unit 251.

The first substrate 240 may include a via-hole 241 formed on a predetermined area of a lower side of the first substrate. The via-hole 241 may penetrate through the first substrate 240, and may connect, to an external side of an electrode. For example, the external side of an electrode may include a first lower portion electrode 263 and a first upper portion electrode 265, laminated on the first substrate 240. The electrode may be connected to the first resonance frequency measuring unit 245, through an electrode pad formed in the via-hole 241. In the example, the first substrate 240 may be a silicon substrate. An insulation layer 243 corresponding to an insulating material may be formed in the via-hole 241 to expose a predetermined area of the electrode pad.

The second substrate 250 may include an air cavity in a predetermined area of a lower side of the second substrate 250, and may be connected to the first substrate 240. In one example, the second substrate 250 may be connected to the first substrate 240 using a bonding metal. In another example, the second substrate 250 may be connected to the first substrate 240 using a polymer as a bonding material. In still another example, the first substrate 240 may be connected to the second substrate 250 based on an anodic bonding scheme or eutectic bonding scheme, by providing a voltage between the first substrate 240 and the second substrate 250. The second substrate 250 may include a transparent material, such as glass, a polymer, a ceramic, and the like. In response to a reaction occurring in the first bulk acoustic wave resonance unit 260 being accompanied by a fluorescence phenomenon, the transparent material may allow occurrence of a reaction or an intensity of the reaction to be optically monitored. The second substrate 250 may isolate the first bulk acoustic wave resonance unit 260 from the external environment so that only the sample affects the first bulk acoustic wave resonance unit 260. The second substrate 250 may include the first in-channel and out-channel unit 251. The first in-channel and out-channel unit 251 corresponds to a channel through which the sample including the target material may flow in and out. The first in-channel and out-channel unit 251 may allow the sample to flow in and out from the external side to a second air cavity, through a hole formed in the second substrate 250. The sample reacts with the coated layer 267 in the second air cavity and may affect a resonance frequency.

The first bulk acoustic wave resonance unit 260 may include a first air cavity 261 formed on the top of the first substrate 240 and a first lower portion electrode 263, a first piezoelectric layer 264, a first upper portion electrode 265, and a coated layer 267. The first lower portion electrode 263, the first piezoelectric layer 264, the first upper portion electrode 265, and the coated layer 267 are laminated on a top of the first air cavity 261. The first lower portion electrode 263, the first piezoelectric layer 264, the first upper portion electrode 265, and the coated layer 267 may be laminated in sequential order. Herein, the first lower portion electrode-first piezoelectric layer-first upper portion electrode-coated layer may relate to a structure in which the first lower portion electrode 263, the first piezoelectric layer 264, the first upper portion electrode 265, and the coated layer 267 are sequentially layered on the top of the first air cavity 261. The coated layer 267 may be coated with a base material that reacts with the target material, so that the target material may be sensed from the sample flowing in and out through the first in-channel and out-channel unit 251. For example, the coated layer 267 may be coated with an antigen that reacts with an antibody, as the base material. Thus, the base material is capable of sensing the antibody. The base material may be coated with the antigen before or after the connection of the first substrate 240 and the second substrate 250. The first bulk acoustic wave resonance unit 260 may include a sacrificial layer in which the first air cavity 261 is to be formed, a membrane supporting layer 262 to support the first air cavity 261, the first lower portion electrode 263, the first piezoelectric layer 264, the first upper portion electrode 265, a protective layer 266 to protect an electrode with an insulating material and the coated layer 267. The insulating material may prevent signal distortion. The first air cavity 261 may be filled with a material having a high dielectric constant. For example, the high dielectric constant material may include air, an inert gas, silicon dioxide ($SiO_2$), silicon nitride ($Si_3N_4$), poly-silicon, a polymer, and the like.

The first resonance frequency measuring unit 245 may measure a changed resonance frequency that is changed due to a reaction between the sample and the coated layer 267, through the first lower portion electrode 263 and the first upper portion electrode 265. The first resonance frequency measuring unit 245 may provide a resonance frequency (RF) signal to the lower portion electrode 263 and the first upper portion electrode 265. Thus, the first resonance frequency measuring unit 245 may measure the changed resonance frequency, which corresponds to a frequency in response to resonance occurring in the first piezoelectric layer 264. The first resonance frequency measuring unit 245 may be connected to the first lower portion electrode 263 and the first upper portion electrode 265, through the electrode pad formed in the via-hole 241.

Referring to FIG. 2B, the reference BAWR 220 includes a third substrate 280, a fourth substrate 290, a second bulk acoustic wave resonance unit 270, and a second resonance frequency measuring unit 281.

The fourth substrate 290 may isolate the second bulk acoustic wave resonance unit 270 from the external environment. Thus, the reference BAWR 220 may measure a reference resonance frequency through the second resonance frequency measuring unit 281. The reference resonance frequency may be measured when the reference BAWR 220 has not reacted with the sample.

The third substrate 280 may include a via-hole formed in a predetermined area of a lower side of the third substrate 280. The via-hole may penetrate through the third substrate 280, and may connect an electrode laminated on a top of the third substrate 280 to an external side.

The second bulk acoustic wave resonance unit 270 may include a third air cavity 271 formed on the top of the third substrate 280 and a second lower portion electrode 273, a second piezoelectric layer 274, and a second upper portion electrode 275 which are laminated on a top of the third air cavity 271. The second bulk acoustic wave resonance unit 270 may include a sacrificial layer in which the third air cavity 271 is to be formed, a membrane supporting layer 272 to support the third air cavity 271, the second lower portion electrode 273, the second piezoelectric layer 274, the second upper portion electrode 275, and a protective layer 276 to protect an electrode with an insulating material. In other words, the second bulk acoustic wave resonance unit 270 may be manufactured to have a form that substantially corresponds with the form of the first bulk acoustic wave resonance unit 260. The second piezoelectric layer 274 and the first piezoelectric layer 264 may be manufactured to have a substantially equal thickness, using substantially the same piezoelectric material. The difference between the first and second bulk acoustic wave resonance units 260 and 270 include that the first bulk acoustic wave resonance unit 260 may further include the coated layer 267, and the coated layer 267 may react with the sample. The third air cavity 271 may be filled with a material having a high dielectric constant. The high dielectric constant material may include air, inert gas, $SiO_2$, $Si_3N_4$, poly-silicon, a polymer, and the like. The second lower portion electrode 273 and the second upper portion electrode 275 may include a conductive material. The conductive material may include gold (Au), molybdenum (Mo), ruthenium (Ru), aluminum (Al), platinum (Pt), titanium (Ti), tungsten (W), palladium (Pd), chromium (Cr), nickel (Ni), and the like. The piezoelectric material used for the second piezoelectric layer 274 may include zinc oxide (ZnO), AlN, quartz, and the like.

The fourth substrate 290 may include an air cavity on a predetermined area of a lower side of the fourth substrate 290. In one example, the fourth substrate 290 may be connected to the third substrate 280. In another example, the fourth substrate 290 may be connected to the third substrate 280 using a bonding metal. The fourth substrate 290 may isolate the second bulk acoustic wave resonance unit 270 from an external environment.

The second resonance frequency measuring unit 281 may measure the reference resonance frequency, through the second lower portion electrode 273 and the second upper portion electrode 275. The second resonance frequency measuring unit 281 may provide an RF signal to the second lower portion electrode 273 and the second upper portion electrode 275 to measure the reference resonance frequency. In other words, the reference resonance frequency may be a frequency in response to resonance occurring in the second piezoelectric layer 274. The second resonance frequency measuring unit 281 may be connected to the second lower portion electrode 273 and the second upper portion electrode 275, through an electrode pad formed in a via-hole.

A structure of a BAWR sensor of FIG. 2C may include a second in-channel and out-channel unit 291 in the reference BAWR 220, when compared to the structure of the BAWR sensor of FIG. 2B.

In response to the BAWR sensor measuring a reference resonance frequency under a predetermined condition, a material providing the predetermined condition may be injected to a predetermined cavity area of the fourth substrate 290. In this example, the second in-channel and out-channel unit 291 may be a channel through which the material providing the predetermined condition flows in and out. As an example, to sense a predetermined antigen-antibody reaction, a buffer or a solution may be injected to both the signal BAWR 210 and the reference BAWR 220, and an antigen and/or an antibody may be injected to the signal BAWR 210. For example, the antigen may be injected to the signal BAWR 210 and the reference BAWR 220, and the antibody may be injected to only the signal BAWR 210. As another example, the predetermined gas may be injected through a channel. Subsequently, a reaction may be sensed by injecting another gas to only the signal BAWR 210

Even though the sample is injected to the reference BAWR 220, only the signal BAWR 210 may be able to measure a changed resonance frequency because the signal BAWR 210 having the coated layer 267 may sense the sample.

A structure of a BAWR sensor of FIG. 2D may include the signal BAWR 210 and the reference BAWR 220 on the same substrate.

Referring to FIG. 2D, the signal BAWR 210 may include the first bulk acoustic wave resonance unit 260, a first resonance frequency measuring unit 295, and the reference BAWR 220 may include the second bulk acoustic wave resonance unit 270 and a second resonance frequency measuring unit 296, substantially the same as the structure of FIG. 2B. In this example, the first bulk acoustic resonance unit 260 and the second bulk acoustic resonance unit 270 may be formed on the same substrate, the same substrate being a first substrate 294. A second substrate 293 may include an air cavity formed on a predetermined area of a lower side of the second substrate 293, and the second substrate 293 may be connected to the first substrate 294. The first bulk acoustic wave resonance unit 260 and the second bulk acoustic wave resonance unit 270 may be located in the air cavity on the lower side of the second substrate 293. The second substrate 293 may include an in-channel and an out-channel unit 292. The in-channel and the out-channel unit 292 may be a channel through which the sample including the target material flows in and out. The sample including the target material may react with the coated layer 267 of the first bulk acoustic wave resonance unit 260, so that a resonance frequency of the first bulk acoustic wave resonance unit 260 changes. The first substrate 294 may include a via-hole formed on a predetermined area of a lower side of the first substrate 294. The via-hole may be formed to penetrate through the first substrate 294, and may connect an electrode laminated on a top of the first substrate 294 to an external side. In one example, the electrode may be connected to the first resonance frequency measuring unit 295 and the second resonance frequency measuring unit 296, through an electrode pad generated in the via-hole. Here, the first resonance frequency measuring unit 295 may measure the changed resonance frequency that is changed due to the reaction between the sample and the coated layer 267 of the first bulk acoustic wave resonance unit 260, through a first lower portion electrode and a first upper portion electrode. The second resonance frequency measuring unit 296 may measure a reference resonance frequency, through a second lower portion electrode and a second upper portion electrode.

Figure 3A:
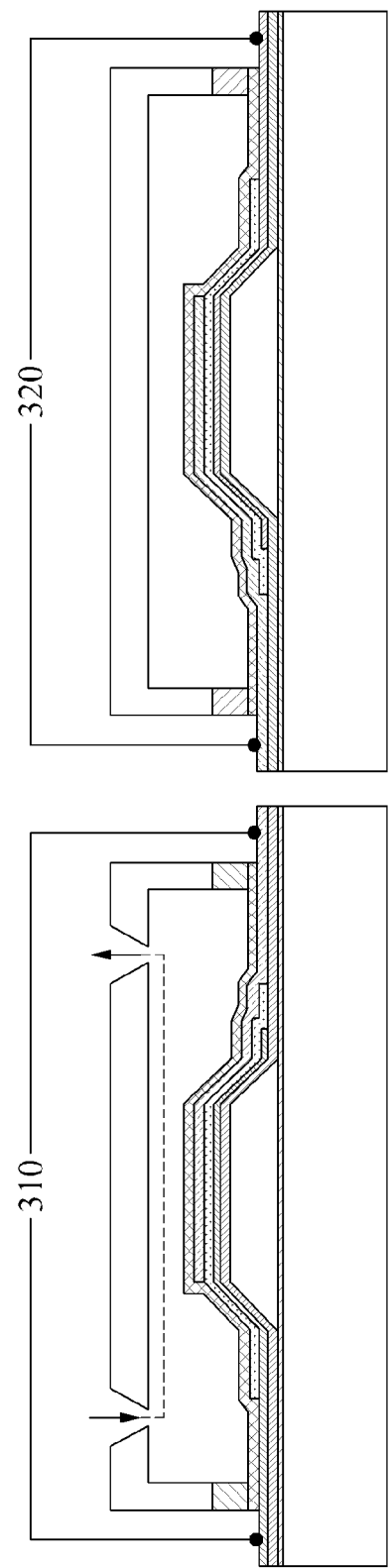
FIGS. 3A through 3C are diagrams illustrating another example of a structure of a BAWR sensor.
Figure 3B:
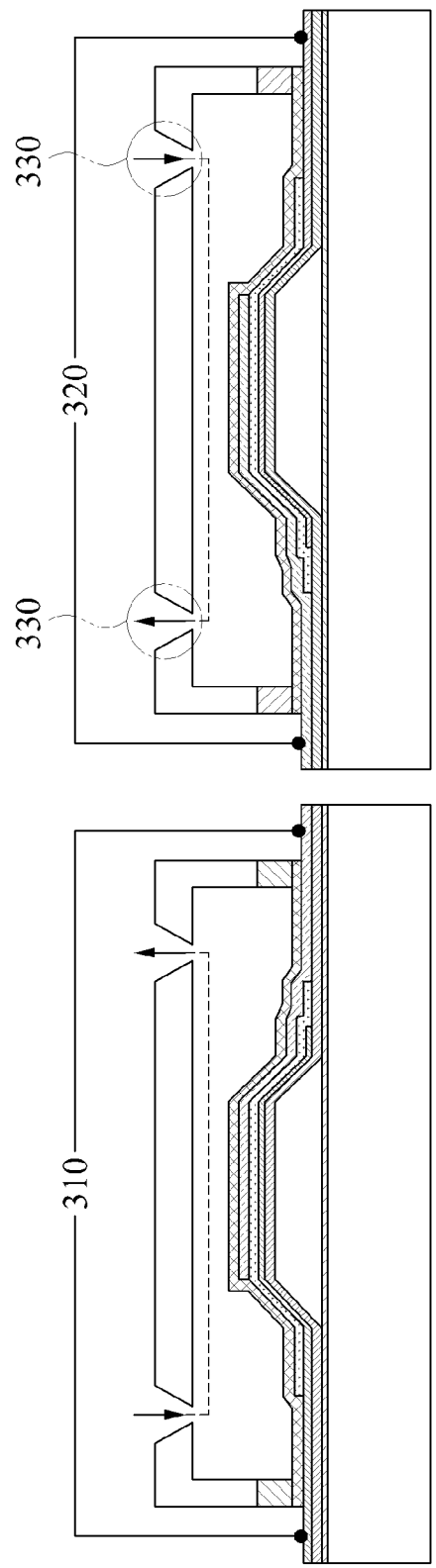
Figure 3C:
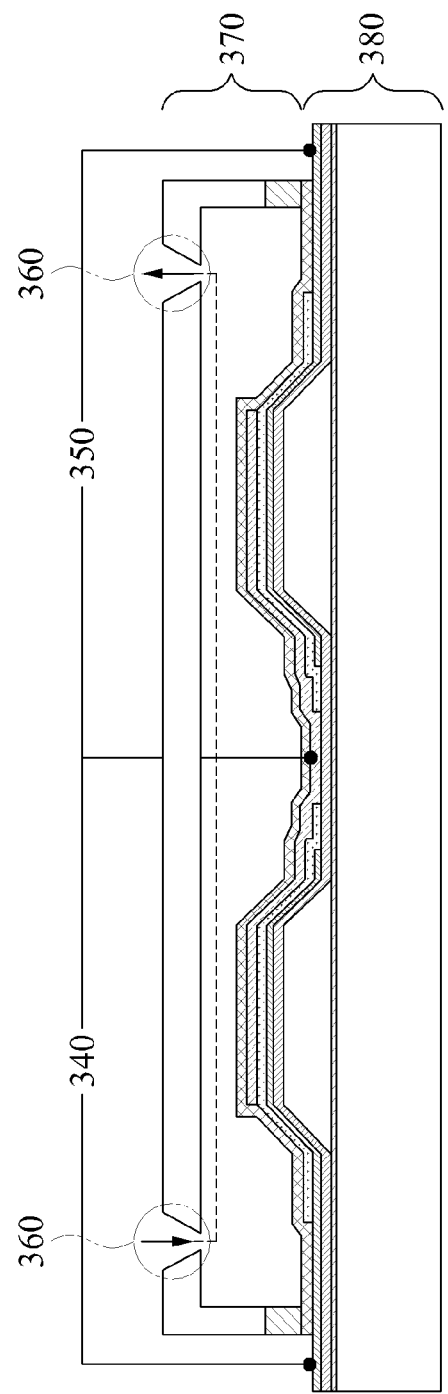

FIGS. 3A through 3C illustrate another example of a structure of a BAWR sensor.

A structure of a BAWR sensor of FIG. 3A includes a first resonance frequency measuring unit 310 and a second resonance frequency measuring unit 320 replacing the first resonance frequency measuring unit 245 and the second resonance frequency measuring unit 281 of the BAWR sensor of FIG. 2B.

The first resonance frequency measuring unit 310 may be connected to the first lower portion electrode 263 and the first upper portion electrode 265. The first lower portion electrode 263 and the first upper portion electrode 265 may be formed by patterning a conductive material on the top of the first substrate 240 and an external side of the second substrate 250. The second resonance frequency measuring unit 320 may be connected to the second lower portion electrode 273 and the second upper portion electrode 275. The second lower portion electrode 273 and the second upper portion electrode 275 may be formed by patterning a conductive material on the top of the third substrate 280 and an external side of the fourth substrate 290. The first resonance frequency measuring unit 310 may be connected to the first lower portion electrode 263 and the first upper portion electrode 265. Thus, the first resonance frequency measuring unit 310 may measure a changed resonance frequency without using the via-hole in the first substrate 240. The second resonance frequency measuring unit 320 may be connected to the second lower portion electrode 273 and the second upper portion electrode 275. Thus, the second resonance frequency measuring unit 320 may measure a reference resonance frequency without using a via-hole in the third substrate 280. In this example, the second substrate 250 may include the isolation layer 266 to prevent signal distortion due to contact between a target material and the first upper portion electrode 265 of the first bulk acoustic wave resonance unit 260. The fourth substrate 290 may include an isolation layer 276 to isolate the second bulk acoustic wave resonance unit 270 from an external environment.

A structure of a BAWR sensor of FIG. 3B may further include a second in-channel and out-channel unit 330 in the reference BAWR 220 of the BAWR sensor of FIG. 3A.

In response to the BAWR sensor measuring a reference resonance frequency under a predetermined condition, a material providing the predetermined condition may be injected to a predetermined cavity area of the fourth substrate 290. In this example, the fourth substrate 290 may include the second in-channel and out-channel unit 330, and the second in-channel and out-channel unit 330 may be a channel through which the material providing the predetermined condition may flow in and out.

A structure of a BAWR sensor of FIG. 3C may include the signal BAWR 210 and the reference BAWR 220 of the BAWR sensor of FIG. 2A on the same substrate.

Referring to FIG. 3C, the signal BAWR 210 may include the first bulk acoustic wave resonance unit 260 and a first resonance frequency measuring unit 340, and the reference BAWR 220 may include the second bulk acoustic wave resonance unit 270 and a second resonance frequency measuring unit 350. In this example, the first bulk acoustic wave resonance unit 260 and the second bulk acoustic wave resonance unit 270 may be formed on the same substrate, the same substrate being a first substrate 380. A second substrate 370 may include an air cavity formed on a predetermined area of a lower side of the second substrate 370, and the second substrate 370 may be connected to the first substrate 380. The first bulk acoustic wave resonance unit 260 and the second bulk acoustic wave resonance unit 270 may be placed in the air cavity on the lower side of the second substrate 370. The second substrate 370 may include an in-channel and out-channel unit 360. The in-channel and out-channel unit 360 may be a channel through which a sample including a target material may flow in and out. The sample including the target material may react with the coated layer 267 of the first bulk acoustic wave resonance unit 260. Thus, a resonance frequency of the first bulk acoustic wave resonance unit 260 may change.

As an example, the first resonance frequency measuring unit 340 may be connected to a first lower portion electrode and a first upper portion electrode formed by patterning a conductive material on a top of the first substrate 380 and an external side of the second substrate 370 of the first bulk acoustic wave resonance unit 260. The second resonance frequency measuring unit 350 may be connected to a second lower portion electrode and a second upper portion electrode formed by patterning a conductive material on the top of the first substrate 380 and the external side of the second substrate 370 of the second bulk acoustic wave resonance unit 270. The first resonance frequency measuring unit 340 may be connected to the first lower portion electrode and the first upper portion electrode. thus, the first resonance frequency measuring unit 340 may measure the changed resonance frequency without using a via-hole in the first substrate 380. The second resonance frequency measuring unit 350 may be connected to the second lower portion electrode and the second upper portion electrode. Thus, the second resonance frequency measuring unit 350 may measure the changed resonance frequency without using the via-hole in the first substrate 380. In this example, the second substrate 370 may use the isolation layer 266 so as to separate the first bulk acoustic wave resonance unit 260 and the second bulk acoustic wave resonance unit 270 from an external environment.

FIGS. 4A through 4D illustrate still another example of a structure of a BAWR sensor.

Figure 4A:
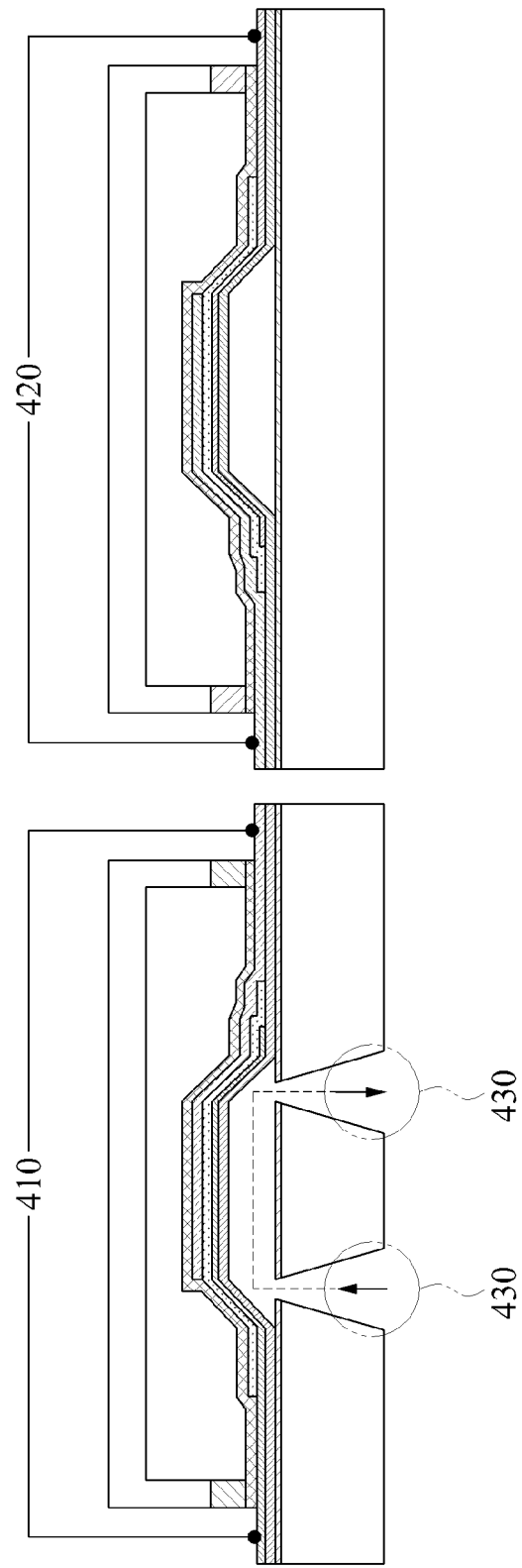
FIGS. 4A through 4D are diagrams illustrating still another example of a structure of a BAWR sensor.

A structure of BAWR sensor of FIG. 4A may include a first in-channel and out-channel unit 430 replacing the first in-channel and out-channel unit 251 of the BAWR sensor of FIG. 3A.

The first in-channel and out-channel unit 430 may allow a sample including a target material to flow in and out from an external side to the first air cavity 261, through a via-hole formed on the first substrate 240. In this example, a coated layer 267 may be located under the first lower portion electrode 263. In another aspect, the coated layer 267 may be sandwiched between the first lower portion electrode 263 and the first air cavity 261. The sample injected through the first in-channel and out-channel unit 430 may react with the coated layer 267 located under the first lower portion electrode 263. Thus, a resonance frequency of the first bulk acoustic wave resonance unit 260 may change. With the structure of the BAWR of FIG. 4A, the reaction with the sample occurs at the top of the first bulk acoustic wave resonance unit 260 and under the first bulk acoustic wave resonance unit 260. Thus, the reaction occurs in the first bulk acoustic wave resonance unit 260.

Figure 4B:
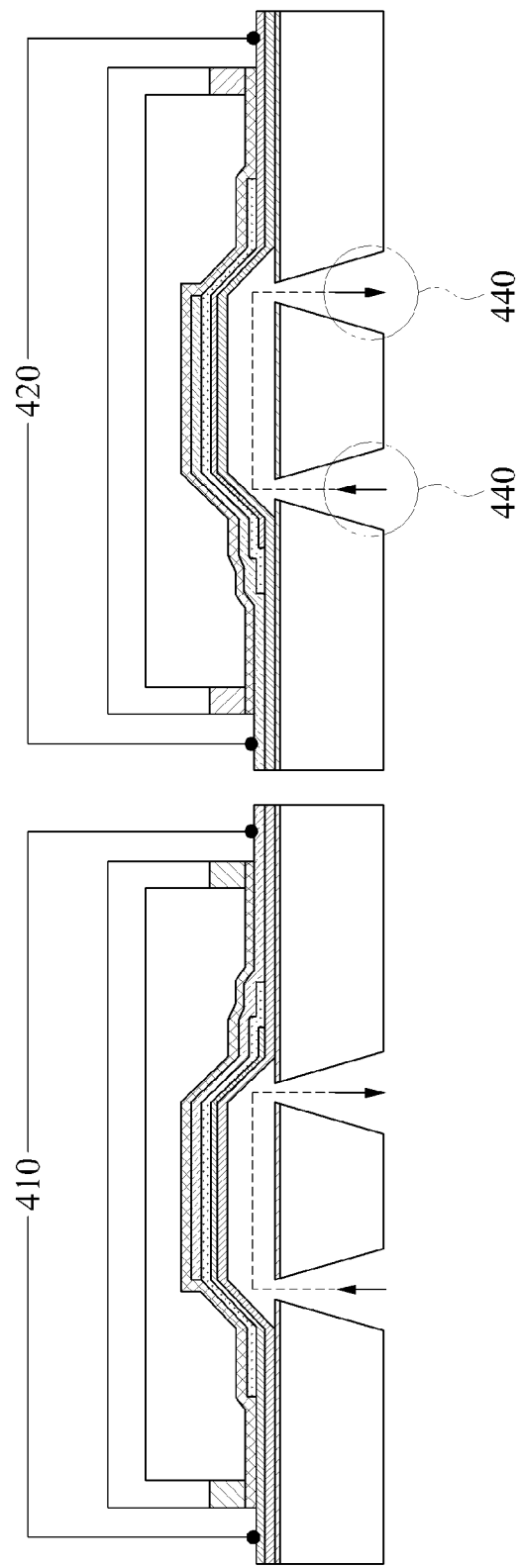

A structure of a BAWR sensor of FIG. 4B may further include a second in-channel and out-channel unit 440 in the reference BAWR 220 of the BAWR sensor of FIG. 4A. The second in-channel and out-channel unit 440 may be located in the third substrate 280.

For example, when the BAWR sensor measures a reference resonance frequency under a predetermined condition, a material providing the predetermined condition may be injected into the third air cavity 271. In this example, the second in-channel and out-channel unit 440 may be a channel through which the material providing the predetermined condition may flow in and out. The second in-channel and out-channel unit 440 may allow a sample including a target material to flow in and out from an external side to the third air cavity 271, through a hole formed on the third substrate 280 corresponding to a lower portion of the third air cavity 271.

Figure 4C:
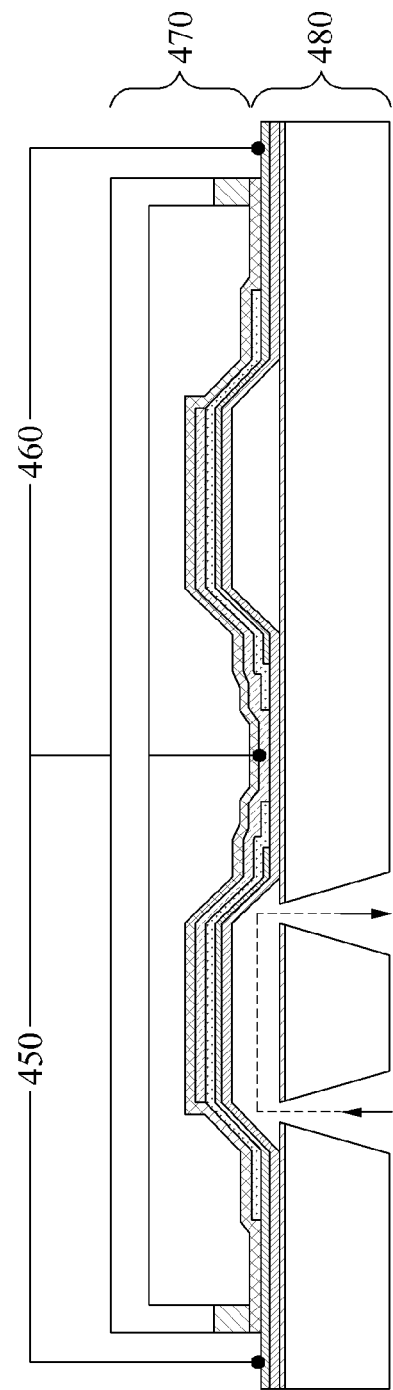

A structure of a BAWR sensor of FIG. 4C may include the signal BAWR 210 and the reference BAWR 220 of the BAWR sensor of FIG. 4A on the same substrate.

Referring to FIG. 4C, the signal BAWR 210 may include the first bulk acoustic wave resonance unit 260 and a first resonance frequency measuring unit 450, and the reference BAWR 220 may include the second bulk acoustic wave resonance unit 270 and a second resonance frequency measuring unit 460. Here, the first BAWR 260 and the second bulk acoustic wave resonance unit 270 may be formed on the same substrate, the same substrate being a first substrate 480. A second substrate 470 may include an air cavity formed on a predetermined area of a lower side of the second substrate 470, and the second substrate 470 may be connected to the first substrate 480. The first bulk acoustic wave resonance unit 260 and the second bulk acoustic wave resonance unit 270 may be placed in the air cavity on the lower side of the second substrate 470. The first substrate 470 may include a first in-channel and out-channel unit. The first in-channel and out-channel unit may allow a sample including a target material to flow in and out from an external side to the first air cavity, through a hole formed in the first substrate 480 corresponding to a lower portion of the first air cavity. In this example, a coated layer may be located under a first lower portion electrode. The sample injected through the first in-channel and out-channel unit may react with the coated layer located under the first lower portion electrode. Thus, a resonance frequency may change.

The first resonance frequency measuring unit 450 may be connected to the first lower portion electrode and a first upper portion electrode formed by patterning a conductive material on a top of the first substrate 480 and an external side of the second substrate 470. The second resonance frequency measuring unit 460 may be connected to a second lower portion electrode and a second upper portion electrode formed by patterning a conductive material on the top of the first substrate 480 and the external side of the second substrate 470. Thus, the first resonance frequency measuring unit 450 may measure the changed resonance frequency without using a via-hole in the first substrate 480. Also, the second resonance frequency measuring unit 460 may measure a reference resonance frequency without using the via-hole in the first substrate 480. In this example, the second substrate 470 may include the isolation layer 266 to isolate the first bulk acoustic wave resonance unit 260 and the second bulk acoustic wave resonance unit 270 from an external side.

Figure 4D:
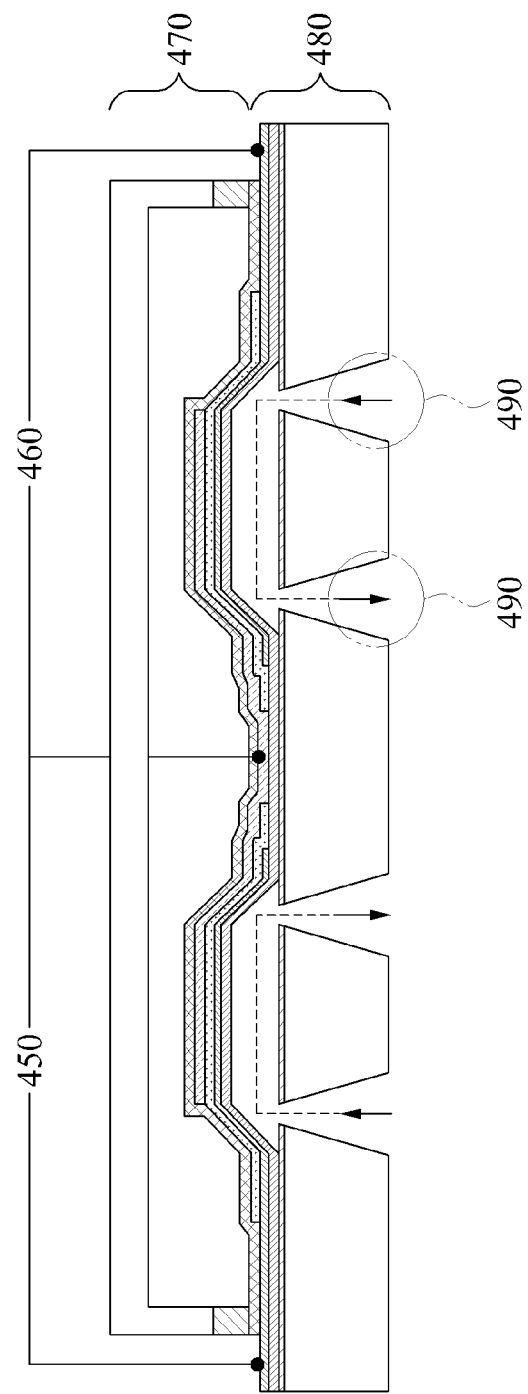

A structure of a BAWR of FIG. 4D may include a second in-channel and out-channel unit 490 in the reference BAWR 220 of the BAWR sensor of FIG. 4C.

In response to the BAWR sensor measuring the reference resonance frequency under a predetermined condition, a material providing the predetermined condition may be injected into an air cavity in a lower side of the second bulk acoustic wave resonance unit 270 via the second in-channel and out-channel unit 490. In this example, the second in-channel and out-channel unit 490 may be a channel through which the material providing the predetermined condition flows in and out. The second in-channel and out-channel unit 490 may allow a sample including a target material to flow in and out from an external side to the air cavity, through a hole formed in the first substrate 480 corresponding to a lower side of the air cavity.

FIGS. 5A through 5D illustrates yet another example of a structure of a BAWR sensor.

Figure 5A:
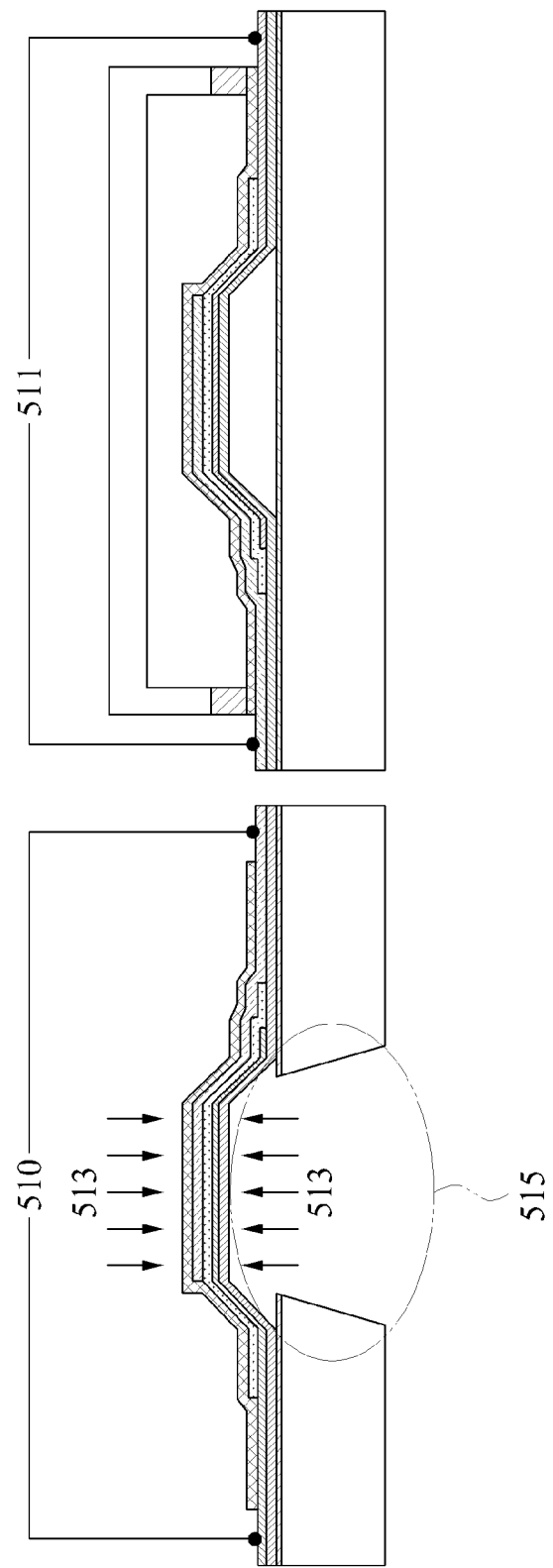
FIGS. 5A through 5D are diagrams illustrating yet another an example of a structure of a BAWR sensor.

A structure of a BAWR sensor of FIG. 5A may exclude the second substrate 250 of the BAWR sensor of FIG. 3A, and may include, in the first substrate 240, a hole 515 formed so that the lower side of the first bulk acoustic wave resonance unit 260 may be exposed to an external environment.

A top and a bottom of the first bulk acoustic wave resonance unit 260 may be wholly exposed to the external environment and thus, a resonance frequency may change based on a change in the external environment. For example, the change in the external environment may include a change in a pressure, a biochemical material, air, a temperature, and the like. The first bulk acoustic wave resonance unit 260 may sense the change in the external environment, through the hole 515 formed in the first substrate 240. The hole 515 enables the lower side of the first bulk acoustic wave resonance unit 260 to be exposed to the external environment. In one example, a coated layer may be located on top of the first upper portion electrode 265. In another example, the coated layer may be located under the first lower portion electrode 263. The coated layer may sense a change in the external environment, using a base material coating the coated layer.

A first resonance frequency measuring unit 510 may be connected to the first lower portion electrode 263 and the first upper portion electrode 265. A second resonance frequency measuring unit 511 may be connected to the second lower portion electrode 273 and the second upper portion electrode 275 formed by patterning a conductive material on a top of the third substrate 280 and an external side of the fourth substrate 290.

Figure 5B:
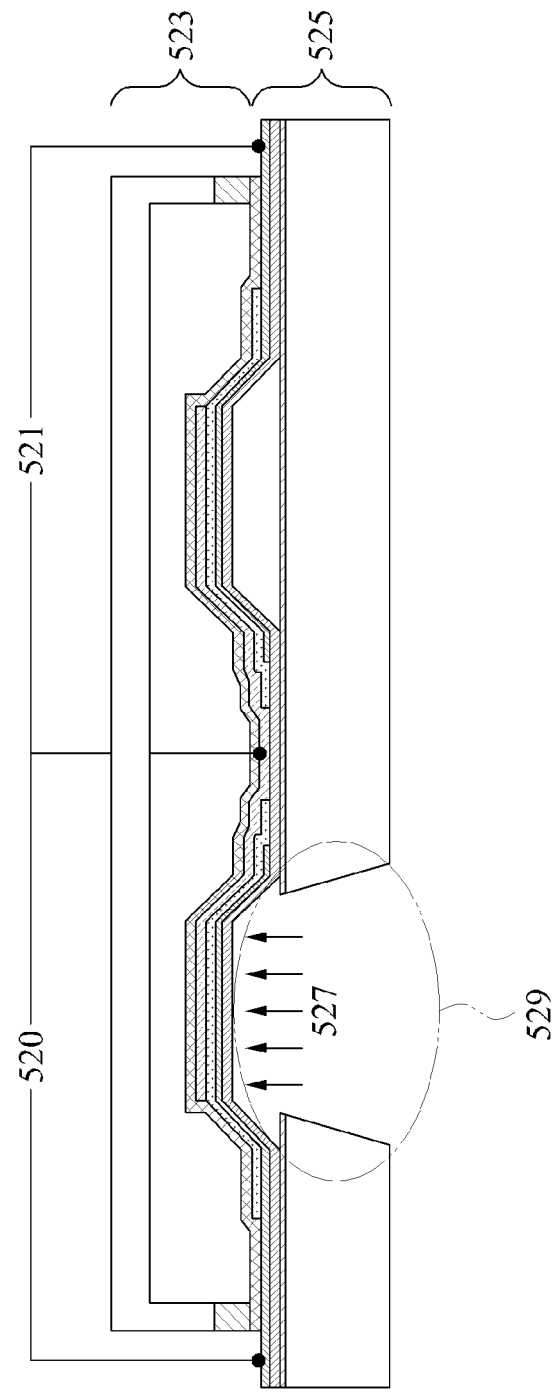

A structure of a BAWR sensor of FIG. 5B may include the signal BAWR 210 and the reference BAWR 220 of the BAWR sensor of FIG. 5A on the same substrate.

Referring to FIG. 5B, the signal BAWR 210 may include the first bulk acoustic wave resonance unit 260 and a first resonance frequency measuring unit 520. The reference BAWR 220 may include the second bulk acoustic wave resonance unit 270 and a second resonance frequency measuring unit 521. In this example, the first bulk acoustic wave resonance unit 260 and the second bulk acoustic wave resonance unit 270 may be formed on the same substrate, the same substrate being a first substrate 525. A second substrate 523 may include an air cavity formed on a predetermined area of a lower side of the second substrate 523. The second substrate may be connected to the first substrate 525. The first bulk acoustic wave resonance unit 260 and the second bulk acoustic wave resonance unit 270 may be placed in the air cavity on the lower side of the second substrate 523. The first substrate 525 may include a hole 529. The hole 529 may enable the lower side of the first bulk acoustic wave resonance unit 260 to be exposed to an external environment 527. A resonance frequency may change in the first bulk acoustic wave resonance unit 260, based on a change in the external environment 527.

The first resonance frequency measuring unit 520 may be connected to a first lower portion electrode and a first upper portion electrode formed by patterning a conductive material on a top of the first substrate 525 and an external side of the second substrate 523. The second resonance frequency measuring unit 521 may be connected to a second lower portion electrode and a second upper portion electrode formed by patterning a conductive material on the top of the first substrate 525 and the external side of the second substrate 523. The first resonance frequency measuring unit 520 may measure the changed resonance frequency. The second resonance frequency measuring unit 521 may measure a reference resonance frequency. In this example, the second substrate 523 may use the isolation layer 266 so as to isolate the first acoustic wave resonance unit 260 and the second acoustic wave resonance unit 270 from the external environment.

Figure 5C:
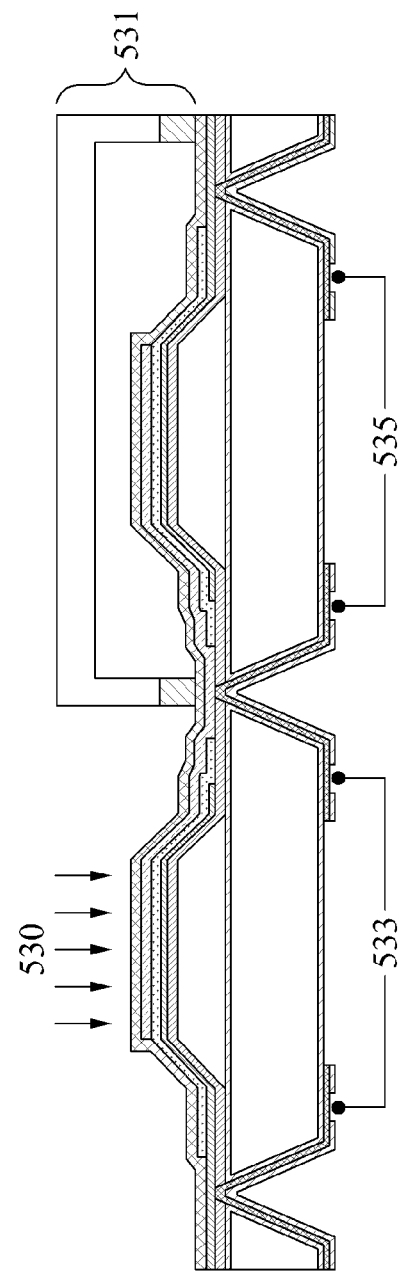

A structure of a BAWR sensor of FIG. 5C may include a second substrate 531 that is connected to only the reference BAWR 220.

The first BAWR resonance unit 260 of the signal BAWR 210 may be exposed to an external environment as shown in a state 530, so that a resonance frequency may change based on a change in the external environment. The second substrate 531 may include an air cavity formed in a predetermined area in a lower side of the second substrate 531, and the second substrate 531 may be connected to the first substrate 294 to conceal the second bulk acoustic wave resonance unit 270 from the external environment.

The first substrate 294 may include a via-hole formed on a predetermined area in a lower side of the first substrate 294. The via-hole may be formed to penetrate through the first substrate 294, and may connect an electrode laminated on a top of the first substrate 294 to an external side. As an example, the electrode may be connected to a first resonance frequency measuring unit 533 and a second resonance frequency measuring unit 535, through an electrode pad formed in the via-hole. The first resonance frequency measuring unit 533 may measure a changed resonance frequency that is changed based on a reaction between the coated layer and the external environment, through a first lower portion electrode and a first upper portion electrode. The second resonance frequency measuring unit 535 may measure a reference resonance frequency, through a second lower portion electrode and a second upper portion electrode.

Figure 5D:
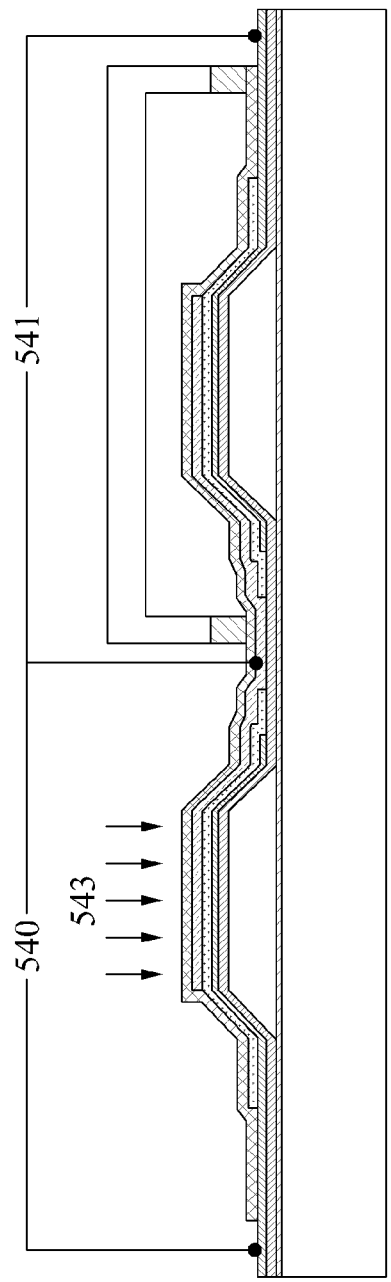

A structure of a BAWR sensor of FIG. 5D may measure a resonance frequency by a different manner from the measuring of FIG. 5C.

A first resonance frequency measuring unit 540 may be connected to a first lower portion electrode and a first upper portion electrode formed by patterning a conductive material on a top of the first substrate and an external side of the second substrate. A second resonance frequency measuring unit 541 may be connected to a second lower portion electrode and a second upper portion electrode formed by patterning a conductive material on the top of the first substrate and the external side of the second substrate. The first resonance frequency measuring unit 540 may be connected to the first lower portion electrode and the first upper portion electrode. The first resonance frequency measuring unit 540 may measure a changed resonance frequency by measuring a change in frequency due to a reaction occurring in the first bulk acoustic wave resonance unit 260, by sensing a change in an external environment. The second resonance frequency measuring unit 541 may be connected to the second lower portion electrode and the second upper portion electrode, and may measure a reference resonance frequency. In this example, the second substrate may include an isolation layer. The isolation layer may isolate the first bulk acoustic wave resonance unit 260 and the second bulk acoustic wave resonance unit 270 from the external environment.

The signal BAWR 210 may include a plurality of bulk acoustic wave resonance units. The plurality of bulk acoustic wave resonance units includes various laminated coated layers. The signal BAWR 210 may detect a plurality of characteristics included in a target material from an injected sample, using base materials with which the various coated layers are coated. The signal BAWR 210 may include a first bulk acoustic wave resonance unit and a second bulk acoustic wave resonance unit that measure changed resonance frequencies.

A first resonance frequency measuring unit may measure a first resonance frequency that is changed due to a first characteristic of the target material in the first bulk acoustic wave resonance unit, and a second resonance frequency measuring unit may measure a second resonance frequency that is changed due to a second characteristic of the target material in the second bulk acoustic wave resonance unit. The first characteristic may be different from the second characteristic.

The sensing unit may detect the first characteristic of the target material based on the measured first resonance frequency and a corresponding reference resonance frequency. That is, the sensing unit may detect the second characteristic of the target material based on the measured second resonance frequency and a corresponding reference resonance frequency. The sensing unit may detect characteristics of the target material from a database based on a variance of a resonance frequency.

The sensor may be included in a pharmaceutical measurement analysis device or a chemical analysis device.

A number of example embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A bulk acoustic wave resonator (BAWR) sensor, comprising:
   a signal BAWR comprising
      a first substrate comprising a first via-hole formed in a lower side of the first substrate and a second via-hole formed in the lower side of the first substrate;
      a first bulk acoustic wave resonance unit comprising a first air cavity formed on a top of the first substrate, a first lower portion electrode formed on top of the first air cavity, a first piezoelectric layer formed on top of the first lower portion electrode, a first upper portion electrode formed one top of the first piezoelectric layer, and a first coated layer, and
      a first resonance frequency measuring unit configured to measure a resonance frequency modified by the sample using the first lower portion electrode and the first upper portion electrode, wherein the first resonance frequency measuring unit is connected to the first lower portion electrode through a first electrode pad within the first via-hole, and is connected to the first upper portion electrode through a second electrode pad within the second via-hole;
   a reference BAWR configured to measure a reference resonance frequency without reaction with an external environment; and a sensing unit configured to sense the target material, based on the first modified resonance frequency and the reference resonance frequency.

2. The BAWR sensor of claim 1, wherein:
the signal BAWR comprises:
a second substrate comprising a second air cavity formed on a predetermined area of a lower side of the second substrate, and connected to the first substrate;
a first in-channel through which a sample including the target material flows in; and
a first out-channel through which the sample including the target material flows out, and
the reference BAWR comprises:
a third substrate;
a second bulk acoustic wave resonance unit comprising a third air cavity formed on a top of the third substrate, a second lower portion electrode formed on a top of the third air cavity, a second piezoelectric layer formed on top of the second lower portion electrode, and a second upper portion electrode formed on top of the second piezoelectric layer;
a fourth substrate comprising a fourth air cavity formed on a predetermined area of a lower side of the fourth substrate, and connected to the third substrate; and
a second resonance frequency measuring unit configured to measure the reference resonance frequency using the second lower portion electrode and the second upper portion electrode.

3. The BAWR sensor of claim 2, wherein the first coated layer is coated with a base material configured to react with the target material to sense the target material from the sample.

4. The BAWR sensor of claim 2, wherein the first coated layer is located on the top of the first upper portion electrode or under the first lower portion electrode.

5. The BAWR sensor of claim 2, wherein the reference acoustic wave resonator further comprises a second in-channel through which the sample including the target material flows in and a second out-channel through which the sample including the target material flows out.

6. The BAWR sensor of claim 2, wherein:
the third substrate comprises a third via-hole formed in a lower side of the third substrate and a fourth via hole formed in the lower side of the third substrate; and
the second resonance frequency measuring unit is connected to the second lower portion electrode through a third electrode pad in the third via-hole, and is connected to the second upper portion electrode through a fourth electrode pad in the fourth via-hole.

7. The BAWR sensor of claim 2, wherein the first in-channel and the first out-channel are further configured to allow the sample to flow in and out from an external side to the second air cavity, through a hole formed on the second substrate.

8. The BAWR sensor of claim 2, wherein the second substrate includes a transparent material so that occurrence of a reaction in the coated layer and an intensity of the reaction are monitored.

9. The BAWR sensor of claim 2, wherein the first substrate and the second substrate are connected to each other based on an anodic bonding scheme or a eutectic bonding scheme.

10. The BAWR sensor of claim 2, wherein the first lower portion electrode, the first piezoelectric layer, the first upper portion electrode, and the first coated layer are sequentially laminated on the top of the first air cavity; and the second lower portion electrode, the second piezoelectric layer, and the second upper portion electrode are sequentially laminated on the top of the third air cavity.

11. The BAWR sensor of claim 1, wherein:
the reference BAWR comprises:
a second bulk acoustic wave resonance unit comprising a second air cavity formed on the top of the first substrate, a second lower portion electrode formed on top of the second air cavity, a second piezoelectric layer formed on top of the second lower portion electrode, and a second upper portion electrode formed on top of the second piezoelectric layer; and
a second resonance frequency measuring unit configured to measure the reference resonance frequency using the second lower portion electrode and the second upper portion electrode, and
the signal BAWR and the reference BAWR comprise:
a second substrate comprising a third air cavity formed on a predetermined area of a lower side of the second substrate, and connected with the first substrate:
an in-channel through which a sample including the target material flows in; and
an out-channel through which the sample including the target material flows out.

12. The BAWR sensor of claim 11, wherein:
the first substrate comprises a third via-hole formed on a predetermined area of a lower side of the first substrate;
the second resonance frequency measuring unit is connected to the second lower portion electrode through a third electrode pad in the third via-hole, and is connected to the second upper portion electrode through the second electrode in the second via-hole.

13. The BAWR sensor of claim 11, wherein the in-channel and the out-channel are further configured to allow the sample to flow in and out from an external side to the third air cavity through a hole formed on the second substrate.

14. The BAWR sensor of claim 1, wherein the reference BAWR comprises:
a second bulk acoustic wave resonance unit comprising a second air cavity formed on the top of the first substrate, a second lower portion electrode formed on top of the second air cavity, a second piezoelectric layer formed on top of the second lower portion electrode, and a second upper portion electrode formed on top of the second piezoelectric layer;
a second substrate comprising a third air cavity formed on a predetermined area of a lower side of the second substrate, and connected to the first substrate so that the second bulk acoustic wave resonance unit is isolated from the external environment; and
a second resonance frequency measuring unit configured to measure the reference resonance frequency, through the second lower portion electrode and the second upper portion electrode.

15. The BAWR sensor of claim 1, wherein the sensing unit comprises:
a database unit configured to store predetermined information corresponding to the modified resonance frequency; and
a matching unit configured to match the modified resonance frequency and the stored predetermined information.

16. The BAWR sensor of claim 1, wherein:
the first air cavity is formed on top of the first substrate so as to detect a first characteristic of the target material;
the signal BAWR comprises:

a second bulk acoustic wave resonance unit comprising a second air cavity formed on the top of the first substrate so as to detect a second characteristic of the target material, a second lower portion electrode formed on top of the second air cavity, a second piezoelectric layer formed on top of the second lower portion electrode, a second upper portion electrode formed on top of the second piezoelectric layer, and a second coated layer; and a second resonance frequency measuring unit configured to measure a second resonance frequency modified by the sample, through the second lower portion electrode and the second upper portion electrode; and the sensing unit detects the first characteristic of the target material based on the first modified resonance frequency, and detects the second characteristic of the target material based on the second modified resonance frequency.

17. The BAWR sensor of claim 1, wherein the sensing unit is further configured to sense the target material based on a difference between the first modified resonance frequency and the reference resonance frequency exceeding a predetermined value.

18. An analysis device comprising:
a bulk acoustic wave resonator (BAWR) sensor unit comprising:
  a signal BAWR configured to measure a resonance frequency that is modified due to a reaction with a target material, the signal BAWR comprising:
    a first substrate comprising a first via-hole formed in a lower side of the first substrate and a second via-hole formed in the lower side of the first substrate;
    a first bulk acoustic wave resonance unit comprising a first air cavity formed on a top of the first substrate, a first lower portion electrode formed on top of the first air cavity, a first piezoelectric layer formed on top of the first lower portion electrode, a first upper portion electrode formed one top of the first piezoelectric layer, and a coated layer; and
    a first resonance frequency measuring unit configured to measure a resonance frequency modified by the sample using the first lower portion electrode and the first upper portion electrode, wherein the first resonance frequency measuring unit is connected to the first lower portion electrode through a first electrode pad within the first via-hole, and is connected to the first upper portion electrode through a second electrode pad within the second via-hole;
  a reference BAWR configured to measure a reference resonance frequency without reaction with the target material; and
  a sensing unit configured to sense the target material, based on the modified resonance frequency and the reference resonance frequency.

19. A bulk acoustic wave resonator (BAWR) sensor, comprising:
a signal BAWR comprising:
  a first substrate;
  a first bulk acoustic wave resonance unit comprising a first air cavity formed on a top of the first substrate, a first lower portion electrode formed on top of the first air cavity, a first piezoelectric layer formed on top of the first lower portion electrode, a first upper portion electrode formed one top of the first piezoelectric layer, and a coated layer; and
  a first resonance frequency measuring unit configured to measure a resonance frequency modified due to a reaction with a target material using the first lower portion electrode and the first upper portion electrode, wherein the first resonance frequency measuring unit is connected to an area of the first lower portion electrode that is exposed above the first substrate, and is connected to an area of the first upper portion electrode that is exposed above the first substrate;
a reference BAWR configured to measure a reference resonance frequency without reaction with an external environment; and
a sensing unit configured to sense the target material, based on the modified resonance frequency and the reference resonance frequency.

20. The BAWR sensor of claim 19, wherein the signal BAWR comprises an in-channel and an out-channel configured to allow a sample including the target material to flow in and out from an external side to the first air cavity through a via-hole formed on the first substrate corresponding to a lower portion of the first air cavity.

21. The BAWR sensor of claim 19, wherein the reference BAWR comprises:
a third substrate;
a second BAWR unit comprising a second air cavity formed on a top of the third substrate, a second lower portion electrode formed on top of the second air cavity, a second piezoelectric layer formed on top of the second lower portion electrode, and a second upper portion electrode formed on top of the second piezoelectric layer;
a fourth substrate comprising a third air cavity formed on a predetermined area of the fourth substrate, and connected to the third substrate; and
a second resonance frequency measuring unit configured to measure the reference resonance frequency, through the second lower portion electrode and the second upper portion electrode.

22. The BAWR sensor of claim 21, wherein the first substrate comprises a hole, corresponding to the first air cavity, formed based on an etching scheme so that an overall area of the signal BAWR is exposed to the external environment.

23. The BAWR sensor of claim 19, wherein:
the signal BAWR comprises:
  a second substrate comprising a second air cavity formed on a predetermined area of a lower side of the second substrate, and connected to the first substrate;
  a first in-channel through which a sample including the target material flows in; and
  a first out-channel through which the sample including the target material flows out; and
the reference BAWR comprises:
  a third substrate;
  a second bulk acoustic wave resonance unit comprising a third air cavity formed on a top of the third substrate, a second lower portion electrode formed on a top of the third air cavity, a second piezoelectric layer formed on top of the second lower portion electrode, and a second upper portion electrode formed on top of the second piezoelectric layer;
  a fourth substrate comprising a fourth air cavity formed on a predetermined area of a lower side of the fourth substrate, and connected to the third substrate; and
  a second resonance frequency measuring unit configured to measure the reference resonance frequency using the second lower portion electrode and the second upper portion electrode, wherein the second resonance frequency measuring unit is connected to an area of the second lower portion electrode that is exposed above the third substrate, and is connected to an area of the second upper portion electrode that is exposed above the third substrate.

24. The BAWR sensor of claim 23, wherein:

the first lower portion electrode and the first upper portion electrode are formed by a conductive material patterned on the top of the first substrate and an external side of the second substrate; and the second lower portion electrode and the second upper portion electrode are formed by a conductive material patterned on the top of the third substrate and an external side of the fourth substrate.

* * * * *